(12) United States Patent
Amano et al.

(10) Patent No.: US 10,849,485 B2
(45) Date of Patent: Dec. 1, 2020

(54) ENDOSCOPE DEVICE USING AN ALTERNATING CURRENT VOLTAGE

(71) Applicant: Sony Olympus Medical Solutions Inc., Tokyo (JP)

(72) Inventors: Kohtaro Amano, Tokyo (JP); Kiyotaka Kanno, Saitama (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 368 days.

(21) Appl. No.: 15/897,179

(22) Filed: Feb. 15, 2018

(65) Prior Publication Data

US 2018/0256016 A1 Sep. 13, 2018

(30) Foreign Application Priority Data

Mar. 13, 2017 (JP) .................................. 2017-047787

(51) Int. Cl.
| | |
|---|---|
| *A61B 1/00* | (2006.01) |
| *A61B 1/04* | (2006.01) |
| *A61B 1/05* | (2006.01) |
| *A61B 1/12* | (2006.01) |
| *H02M 1/14* | (2006.01) |
| *H02M 7/04* | (2006.01) |

(52) U.S. Cl.
CPC .......... *A61B 1/053* (2013.01); *A61B 1/00027* (2013.01); *A61B 1/00124* (2013.01); *A61B 1/00195* (2013.01); *A61B 1/041* (2013.01); *A61B 1/127* (2013.01); *H02M 1/143* (2013.01); *H02M 7/04* (2013.01)

(58) Field of Classification Search
CPC ......... A61B 1/127; A61B 1/128; A61B 1/042; A61B 1/00195; A61B 1/00124; A61B 1/00066; A61B 1/00027; A61B 1/00018; H02M 1/143; H02M 7/04; H01R 39/10
USPC ........................................................ 600/112
See application file for complete search history.

(56) References Cited

U.S. PATENT DOCUMENTS 4,281,910 A * 8/1981 Takayama ................ A61B 1/04
 348/73
4,318,395 A * 3/1982 Tawara .............. G02B 23/2453
 359/827

(Continued)

FOREIGN PATENT DOCUMENTS

| JP | 59069720 A * 4/1984 ......... G02B 23/2484 |
| JP | 2000-262467 9/2000 |

*Primary Examiner* — John P Leubecker
(74) *Attorney, Agent, or Firm* — Xsensus LLP

(57) ABSTRACT

An endoscope device includes: an endoscope configured to retrieve a subject image in a subject from a tip end, and output the subject image from an eyepiece unit; and a camera head including a mounting unit detachably connected to the eyepiece unit, and configured to pick up the subject image. The eyepiece unit and the mounting unit are connected with each other so as to be able to relatively rotate the endoscope and the camera head around an insertion axis. The eyepiece unit includes an endoscope side terminal. The mounting unit includes a head side terminal that feeds power to the endoscope from the camera head. One of the endoscope side terminal and the head side terminal includes at least three terminals disposed on a virtual circle around the insertion axis, and the other includes at least two terminals disposed on the virtual circle.

20 Claims, 8 Drawing Sheets

(56) References Cited

U.S. PATENT DOCUMENTS

| | | | | |
|---|---|---|---|---|
| 4,697,894 | A * | 10/1987 | Takamura | G02B 23/2476 359/503 |
| 4,797,737 | A * | 1/1989 | Yazawa | A61B 1/042 348/73 |
| 4,851,866 | A * | 7/1989 | Ciarlei | A61B 1/042 348/75 |
| 5,707,340 | A * | 1/1998 | Hipp | A61B 1/00195 285/314 |
| 6,080,101 | A * | 6/2000 | Tatsuno | A61B 1/00124 348/65 |
| 7,364,108 | B2 * | 4/2008 | Kim | A01K 89/00 242/370 |
| 2006/0173245 | A1 * | 8/2006 | Todd | A61B 1/07 600/178 |
| 2014/0221743 | A1 * | 8/2014 | Sugiyama | A61B 1/128 600/109 |
| 2014/0275780 | A1 * | 9/2014 | Feingold | A61B 1/04 600/109 |
| 2015/0062153 | A1 * | 3/2015 | Mihalca | A61B 1/0669 345/604 |
| 2017/0318205 | A1 * | 11/2017 | Duckett, III | H04W 72/0406 |

* cited by examiner

ENDOSCOPE DEVICE USING AN ALTERNATING CURRENT VOLTAGE

CROSS-REFERENCE TO RELATED APPLICATION

The present application claims priority to and incorporates by reference the entire contents of Japanese Patent Application No. 2017-047787 filed in Japan on Mar. 13, 2017.

BACKGROUND

The present disclosure relates to an endoscope device.

In the related art, an endoscope device that picks up an image inside a subject (living body) such as human using an image pickup device, and that observes the inside of the living body has been known (for example, see Japanese Laid-open Patent Publication No. 2000-262467 (FIG. 4)).

The endoscope device disclosed in Japanese Laid-open Patent Publication No. 2000-262467 (FIG. 4) is configured of a head separated type endoscope device. More specifically, the endoscope device includes an endoscope that is to be inserted inside the living body, that retrieves a subject image inside the living body from the tip end, and that outputs the subject image from an eyepiece unit; and a camera head that is detachably connected to the eyepiece unit, and that picks up the subject image. In the endoscope device, power is fed to the camera head from an external light source and a television camera device via the endoscope. Consequently, two endoscope side terminals are disposed in the eyepiece unit. Moreover, a mounting surface of the camera head includes two head side terminals that feed power to the camera head from the endoscope, and that are electrically connected to the two endoscope side terminals in a one-to-one manner. More specifically, the two endoscope side terminals each have a ring shape around the center axis of the endoscope, and are configured of ring-shaped terminals having diameters different from each other. Moreover, the two head side terminals are disposed side by side in the radial direction around the center axis of the endoscope, and are configured of projecting type terminals to be inserted into the two ring-shaped terminals, respectively. In other words, in the endoscope device, the endoscope side terminals and the head side terminals correspond to the relative rotation of the endoscope and the camera head around the center axis of the endoscope, by forming the endoscope side terminals and the head side terminals in the shape described above.

SUMMARY

However, in the endoscope device disclosed in Japanese Laid-open Patent Publication No. 2000-262467 (FIG. 4), the endoscope side terminals and the head side terminals are disposed side by side in the radial direction around the center axis of the endoscope. Thus, the diameters of the endoscope (eyepiece unit) and the camera head need to be increased in the radial direction around the center axis of the endoscope, by taking into account the arrangement of the endoscope side terminals and the head side terminals. In other words, with the endoscope device disclosed in Japanese Laid-open Patent Publication No. 2000-262467 (FIG. 4), the size of the endoscope device is prevented from being reduced.

An endoscope device according to one aspect of the present disclosure may include: an endoscope adapted to be inserted into a subject, and configured to retrieve a subject image in the subject from a tip end, and output the subject image from an eyepiece unit; and a camera head including a mounting unit detachably connected to the eyepiece unit, and configured to pick up the subject image, wherein the eyepiece unit and the mounting unit are connected with each other so as to be able to relatively rotate the endoscope and the camera head around an insertion axis of the endoscope to be inserted into the subject, the eyepiece unit includes an endoscope side terminal, the mounting unit includes a head side terminal that is electrically connected to the endoscope side terminal and that feeds power to the endoscope from the camera head, one of the endoscope side terminal and the head side terminal includes at least three terminals disposed on a virtual circle around the insertion axis, and other of the endoscope side terminal and the head side terminal includes at least two terminals disposed on the virtual circle.

DETAILED DESCRIPTION

Figure 1:
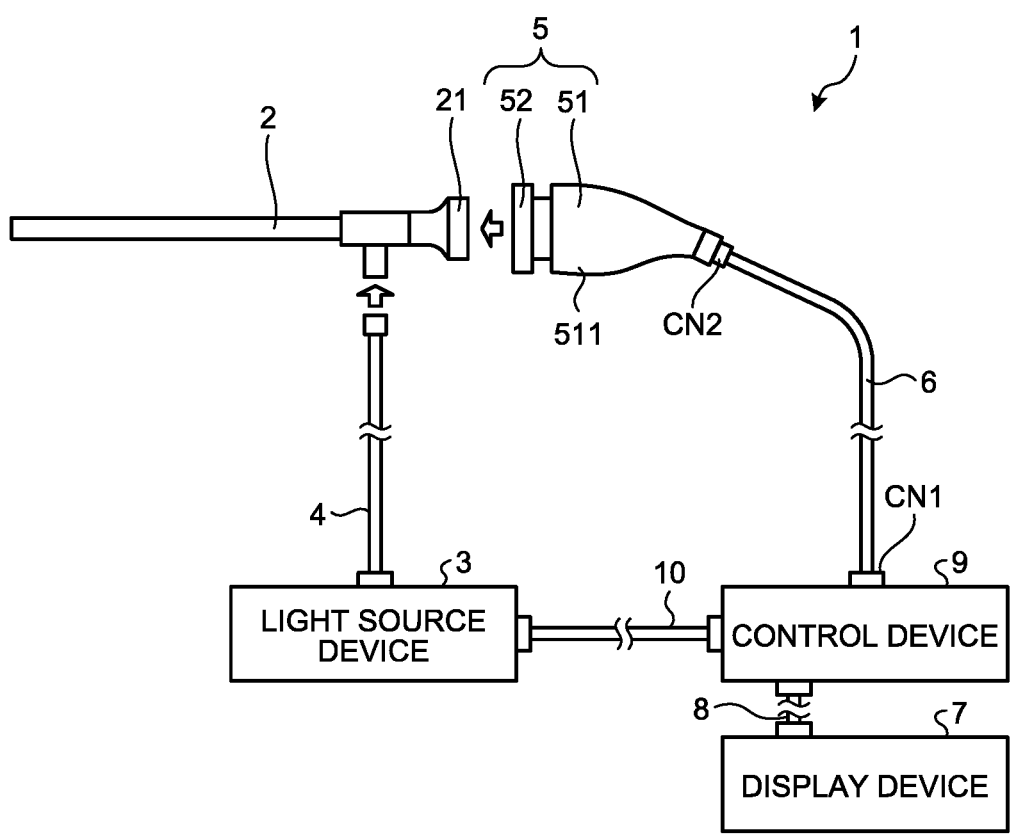
FIG. 1 is a diagram illustrating a schematic configuration of an endoscope device according to the present embodiment.

Hereinafter, a mode for carrying out the present disclosure (hereinafter, an embodiment) will be described with reference to the accompanying drawings. It is to be noted that the present disclosure is not limited to the embodiment to be described below. Moreover, in the drawings, the same reference numerals denote the same components.

Schematic Configuration of Endoscope Device

FIG. 1 is a diagram illustrating a schematic configuration of an endoscope device 1 according to the present embodiment. The endoscope device 1 is used in medical field, and is a device for observing the inside of a living body. As illustrated in FIG. 1, the endoscope device 1 includes an endoscope 2, a light source device 3, a light guide 4, a camera head 5, a first transmission cable 6, a display device 7, a second transmission cable 8, a control device 9, and a third transmission cable 10.

The endoscope 2 is formed of a rigid endoscope. In other words, the endoscope 2 is rigid or at least a part thereof is flexible. The endoscope 2 also has an elongated shape and is to be inserted into the living body. An optical system that is configured of one or a plurality of lenses and that collects a subject image is provided inside the endoscope 2.

In general, for example, the endoscope 2 is placed in an environment where temperature and humidity are controlled such as a treatment room. Consequently, the tip end of the endoscope 2 is exposed to the temperature and humidity such as above before being used. Thus, for example, when the endoscope 2 is inserted into the living body, the optical system disposed inside the endoscope 2 gets fogged by the temperature difference between the room temperature and the body temperature, high humidity environment inside the living body (humidity: about 98 to 100%), and the like. Hence, the view will be significantly reduced.

Thus, a fogging preventing device 11 (see FIG. 4) for preventing the optical system from getting fogged is disposed inside the endoscope 2.

The fogging preventing device 11 includes a heater 111 that generates heat by being energized and that applies the heat to the optical system. The fogging preventing device 11 also includes a temperature sensor 112 that detects temperature of the optical system (see FIG. 4).

An end of the light guide 4 is connected to the light source device 3, and under the control by the control device 9, the light source device 3 supplies light to an end of the light guide 4, to illuminate inside the living body.

An end of the light guide 4 is detachably connected to the light source device 3, and the other end of the light guide 4 is detachably connected to the endoscope 2. The light guide 4 transmits the light supplied from the light source device 3 from one end to the other end, and supplies the light to the endoscope 2. The light supplied to the endoscope 2 is output from the tip end of the endoscope 2, and illuminates the inside of the living body. The light that illuminates the inside of the living body, and that is reflected in the living body (subject image) is collected by the optical system in the endoscope 2.

The camera head 5 includes an air-tight unit 51 (FIG. 1) and a mounting unit 52. The air-tight unit 51 stores therein an image pickup unit (not illustrated) and the like in an air-tight manner. The mounting unit 52 is disposed inside the air-tight unit 51 and is detachably connected to an eyepiece unit 21 (FIG. 1) of the endoscope 2. The camera head 5 then picks up the subject image collected by the endoscope 2, and outputs an image signal (RAW signal) obtained by the image pickup, under the control by the control device 9. For example, the image signal is an image signal of 4K or more. Moreover, the camera head 5 supplies power to the endoscope 2 for driving the fogging preventing device 11 and the like, on the basis of the power supplied from the control device 9.

The detailed configurations of the eyepiece unit 21 and the mounting unit 52, as well as the detailed power feeding structure to the endoscope 2 from the camera head 5 will be described in detail below.

An end of the first transmission cable 6 is detachably connected to the control device 9 via a connector CN1 (FIG. 1), and the other end of the first transmission cable 6 is detachably connected to the camera head 5 via a connector CN2 (FIG. 1). The first transmission cable 6 then transmits an image signal and the like output from the camera head 5 to the control device 9, and transmits a control signal, a synchronization signal, a clock, power, and the like output from the control device 9 to the camera head 5.

The image signal and the like to be transmitted to the control device 9 from the camera head 5 via the first transmission cable 6, may be transmitted using an optical signal. Alternatively, the image signal and the like may be transmitted using an electric signal. The control signal, the synchronization signal, and the clock to be transmitted to the camera head 5 from the control device 9 via the first transmission cable 6 may also be transmitted using the optical signal or the electric signal.

The display device 7 is formed by a display using liquid crystal, an organic electro luminescence (EL), or the like. The display device 7 displays an image on the basis of a video signal from the control device 9, under the control by the control device 9.

An end of the second transmission cable 8 is detachably connected to the display device 7, and the other end of the second transmission cable 8 is detachably connected to the control device 9. The second transmission cable 8 then transmits a video signal processed by the control device 9 to the display device 7.

The control device 9 includes a central processing unit (CPU), and integrally controls the operations of the light source device 3, the camera head 5, and the display device 7.

For example, the control device 9 generates a video signal by performing various processes on an image signal obtained from the camera head 5 via the first transmission cable 6. The control device 9 then outputs the video signal to the display device 7 via the second transmission cable 8. The display device 7 then displays an image on the basis of the video signal. The control device 9 then outputs a control signal and the like to the camera head 5 and the light source device 3, via the first and third transmission cables 6 and 10.

An end of the third transmission cable 10 is detachably connected to the light source device 3, and the other end of the third transmission cable 10 is detachably connected to the control device 9. The third transmission cable 10 then transmits the control signal from the control device 9 to the light source device 3.

Configuration of Eyepiece Unit

Next, a configuration of the eyepiece unit 21 will be described.

It is to be noted that a "tip end" to be described below is an end of the endoscope 2 at the tip end side. Moreover, a "base end" is an end of the endoscope 2 at a side separating from the tip end.

Figure 2A:
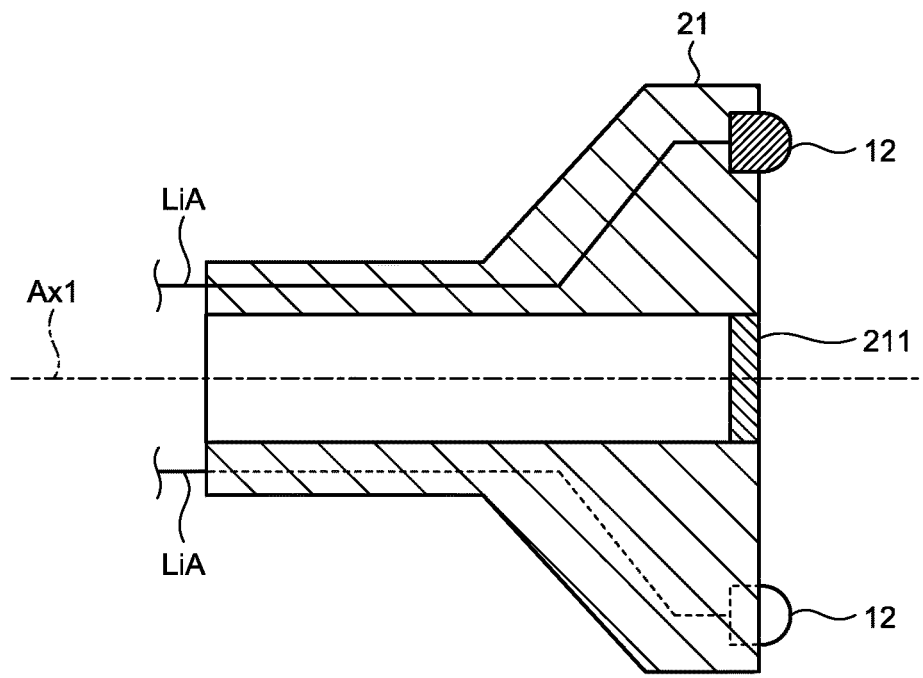
FIG. 2A is a diagram illustrating a configuration of an eyepiece unit.
Figure 2B:
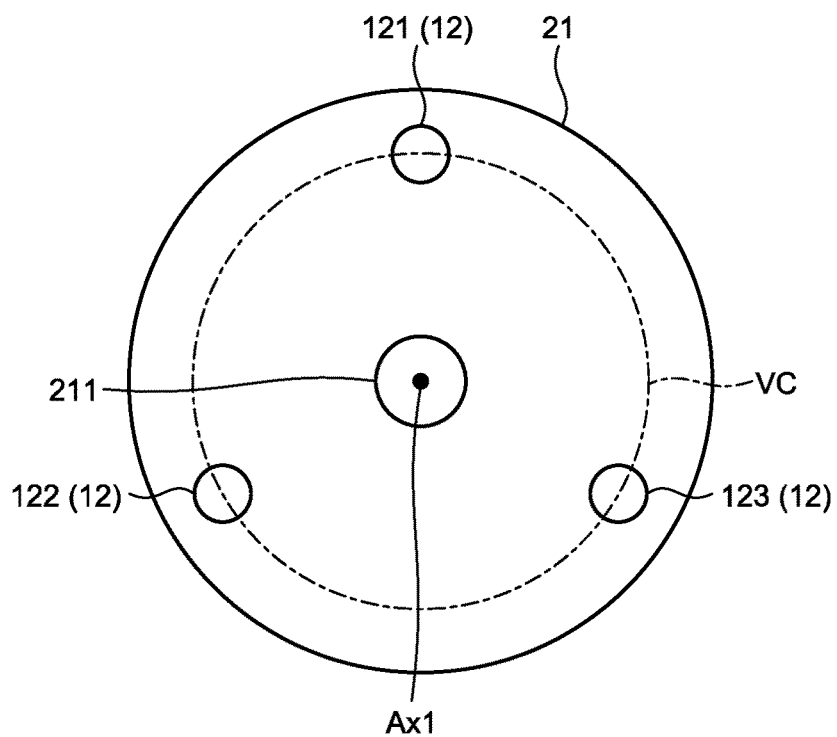
FIG. 2B is a diagram illustrating a configuration of the eyepiece unit.

FIG. 2A and FIG. 2B are diagrams each illustrating a configuration of the eyepiece unit 21. More specifically, FIG. 2A is a sectional view of the eyepiece unit 21 cut at a cross-section along a center axis Ax1 (corresponds to an insertion axis) of the eyepiece unit 21. FIG. 2B is a diagram viewing the eyepiece unit 21 from the base end side.

The eyepiece unit 21 has a substantially cylindrical shape, and is disposed on the base end of the endoscope 2. The eyepiece unit 21 includes an eyepiece optical system 211 (FIG. 2A and FIG. 2B) that outputs a subject image collected by the optical system in the endoscope 2, to the outside from the base end of the eyepiece unit 21. The eyepiece unit 21 is formed in a tapered shape having a diameter increased toward the base end side, and the mounting unit 52 is detachably connected to the increased diameter portion.

As illustrated in FIG. 2A, the end surface of the eyepiece unit 21 at the base end side is a flat surface orthogonal to the center axis Ax1 (a lens optical axis of the eyepiece optical system 211) of the eyepiece unit 21. As illustrated in FIG. 2A or FIG. 2B, an endoscope side terminal 12 is disposed on an end surface at the base end side.

The endoscope side terminal 12 is made of a conductive material such as metal. The endoscope side terminal 12 is also a terminal having a convex shape projecting from the end surface of the eyepiece unit 21 at the base end side, and is embedded in the end surface. More specifically, the sectional surface of the endoscope side terminal 12 cut along a cross-section orthogonal to the center axis Ax1 has a circular shape, and the tip has a semi-circular shape. The endoscope side terminal 12 is electrically connected to a power line LiA (FIG. 2A) wired inside the endoscope 2.

In the present embodiment, as illustrated in FIG. 2B, the endoscope side terminal 12 is configured by three terminals of first to third endoscope side terminals 121 to 123 that are provided in a state of being insulated from each other. The first to third endoscope side terminals 121 to 123 have the same shape, and are disposed so that the projecting dimensions from the end surface of the eyepiece unit 21 at the base end side become the same. Moreover, the first to third endoscope side terminals 121 to 123 are disposed so as to be rotationally symmetric at 120 degrees around the center axis Ax1, on a virtual circle VC around the center axis Ax1. Similarly, corresponding to the first to third endoscope side terminals 121 to 123, the power line LiA is configured by three power lines of first to third power lines LiA1 to LiA3 (see FIG. 4).

Configuration of Mounting Unit

Next, a configuration of the mounting unit 52 will be described.

Figure 3A:
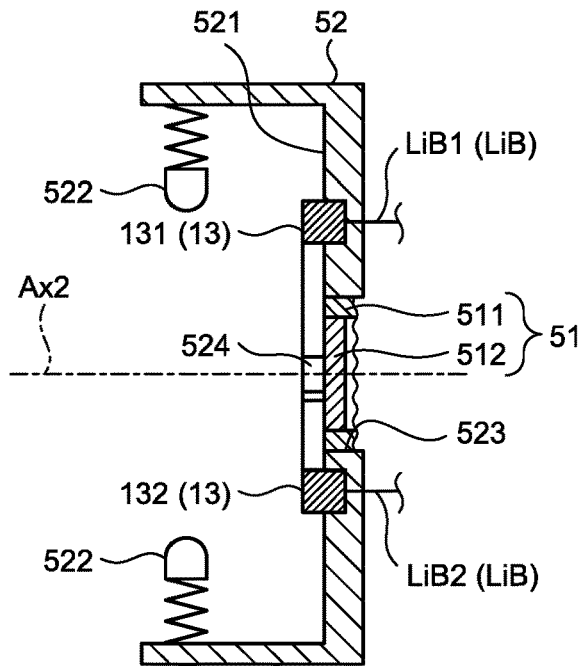
FIG. 3A is a diagram illustrating a configuration of a mounting unit.
Figure 3B:
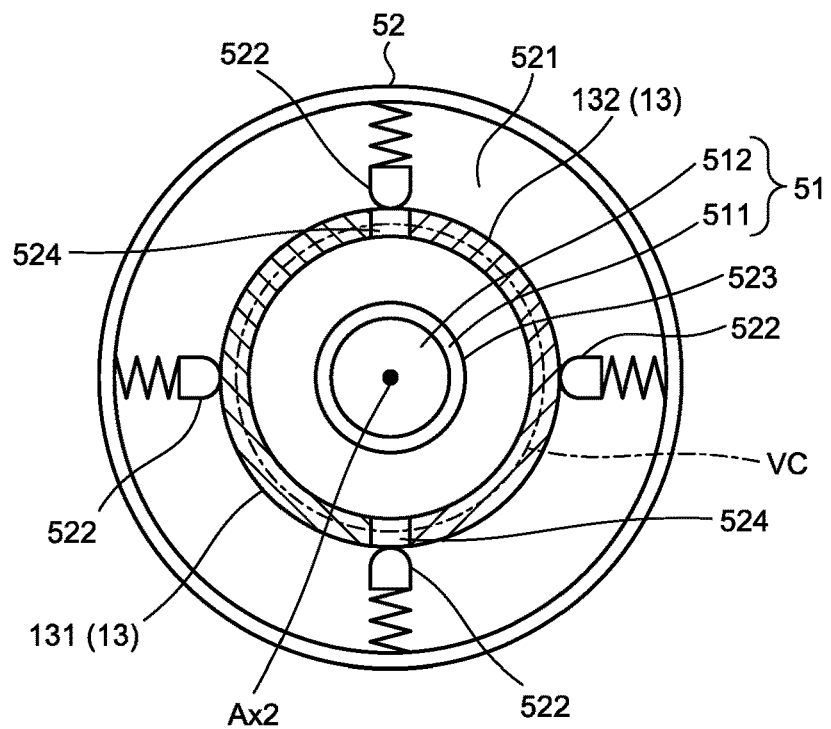
FIG. 3B is a diagram illustrating a configuration of the mounting unit.

FIG. 3A and FIG. 3B are diagrams each illustrating a configuration of the mounting unit 52. More specifically, FIG. 3A is a sectional view of the mounting unit 52 cut at a cross-section along a center axis Ax2 (corresponding to the insertion axis) of the mounting unit 52. FIG. 3B is a diagram viewing the mounting unit 52 from the tip end side.

The mounting unit 52 has a cylindrical shape.

As illustrated in FIG. 3A or FIG. 3B, the mounting unit 52 includes a fitting hole 521 that is recessed toward the base end side and into which the eyepiece unit 21 is fitted, on the end surface at the tip end side. When the eyepiece unit 21 is fitted to the fitting hole 521, the center axes Ax1 and Ax2 match with each other. Moreover, a pressing unit 522 is disposed on the inner peripheral surface of the fitting hole 521.

The pressing unit 522 is elastic so that the pressing unit 522 may move in a direction coming close to or separating from the center axis Ax2. The pressing unit 522 comes into contact with the outer peripheral surface of the eyepiece unit 21, and presses the eyepiece unit 21 toward the right direction in FIG. 3A. In the present embodiment, as illustrated in FIG. 3B, four pressing units 522 are provided. The four pressing units 522 are disposed so as to be rotationally symmetric at 90 degrees around the center axis Ax2.

The endoscope 2 and the camera head 5 may relatively rotate around the center axis Ax1 (Ax2), while the endoscope 2 and the camera head 5 are connected with each other.

In the mounting unit 52, as illustrated in FIG. 3A or FIG. 3B, a communication hole 523 for communicating with the fitting hole 521 as well as for connecting with the air-tight unit 51 is disposed on the end surface at the base end side.

The communication hole 523 is a round hole the center of which matches with the center axis Ax2. A part of the air-tight unit 51 at the tip end side is connected to the communication hole 523. It is to be noted that FIG. 3A and FIG. 3B only illustrate a casing 511 that configures the air-tight unit 51, and an optical device 512 that seals the opening of the casing 511 in an air-tight manner.

In this example, as illustrated in FIG. 3A, the bottom surface of the fitting hole 521 is a flat surface orthogonal to the center axis Ax2. As illustrated in FIG. 3A or FIG. 3B, a head side terminal 13 is disposed on the bottom surface.

The head side terminal 13 is made of a conductive material such as metal, and is embedded in the bottom surface of the fitting hole 521. The head side terminal 13 is electrically connected to a power line LiB (FIG. 3A) wired inside the air-tight unit 51.

In the present embodiment, as illustrated in FIG. 3B, the head side terminal 13 is configured by two terminals of first and second head side terminals 131 and 132 that are disposed in a state of being insulated from each other. The first and second head side terminals 131 and 132 have the same shape, formed in a substantially semi-circular arc shape extending along the virtual circle VC (the same circle as the virtual circle VC illustrated in FIG. 2B) around the center axis Ax2. The surfaces of the first and second head side terminals 131 and 132 at the tip end side are flat and are disposed so as to be flush with each other. The first and second head side terminals 131 and 132 are also disposed so as to be rotationally symmetric at 180 degrees around the center axis Ax2. Similarly, corresponding to the first and second head side terminals 131 and 132, the power line LiB is also configured by two power lines of first and second power lines LiB1 and LiB2 (FIG. 3A).

Moreover, as illustrated in FIG. 3A or FIG. 3B, a projection unit 524 is disposed between the first and second head side terminals 131 and 132 on the virtual circle VC, on the bottom surface of the fitting hole 521. The surface of the projection unit 524 at the tip end side is flat, and the projection unit 524 is disposed so that the flat surface at the tip end side is flush with the surfaces of the first and second head side terminals 131 and 132 at the tip end side. In this example, on the virtual circle VC, the distance between the first and second head side terminals 131 and 132 (length of the projection unit 524 along the virtual circle VC) is substantially the same as the length of the endoscope side terminal 12 along the virtual circle VC (see FIG. 7B). In FIG. 3B, to differentiate the first and second head side terminals 131 and 132 from the projection unit 524, the first and second head side terminals 131 and 132 are shaded with diagonal lines.

The head side terminal 13 is then brought into contact and electrically connected with the endoscope side terminal 12, when the eyepiece unit 21 is connected to the mounting unit 52. In other words, the endoscope side terminal 12 and the head side terminal 13 function as terminals for supplying power to the endoscope 2 from the camera head 5. Moreover, the plane surface formed by the tips of the three endoscope side terminals 12 and the flat surfaces of the two head side terminals 13 at the tip end side function as positioning surfaces of the endoscope 2 relative to the camera head 5 (positioning surface in the center axis Ax1 (Ax2) direction, and positioning surface around the two axes orthogonal to the center axis Ax1 (Ax2) in the rotation direction).

Air-tightness of the endoscope 2 and the camera head 5 needs to be ensured to protect the members to be disposed inside the endoscope 2 and the camera head 5, from chemical liquid used for sterilization treatment such as wiping and immersion, as well as from high-temperature and high-pressure steam by the autoclave process (high-temperature and high-pressure steam sterilization process). When a configuration in which the endoscope side terminal 12 and the head side terminal 13 are simply embedded in the end surface of the eyepiece unit 21 at the base end side and the bottom surface of the fitting hole 521, it is difficult to ensure the air-tightness of the endoscope 2 and the camera head 5.

Consequently, in the present embodiment, the endoscope side terminal 12 and the head side terminal 13 are formed using insert molding.

Power Feeding Structure to Endoscope from Camera Head Next, a power feeding structure to the endoscope 2 from the camera head 5 will be described.

Figure 4:
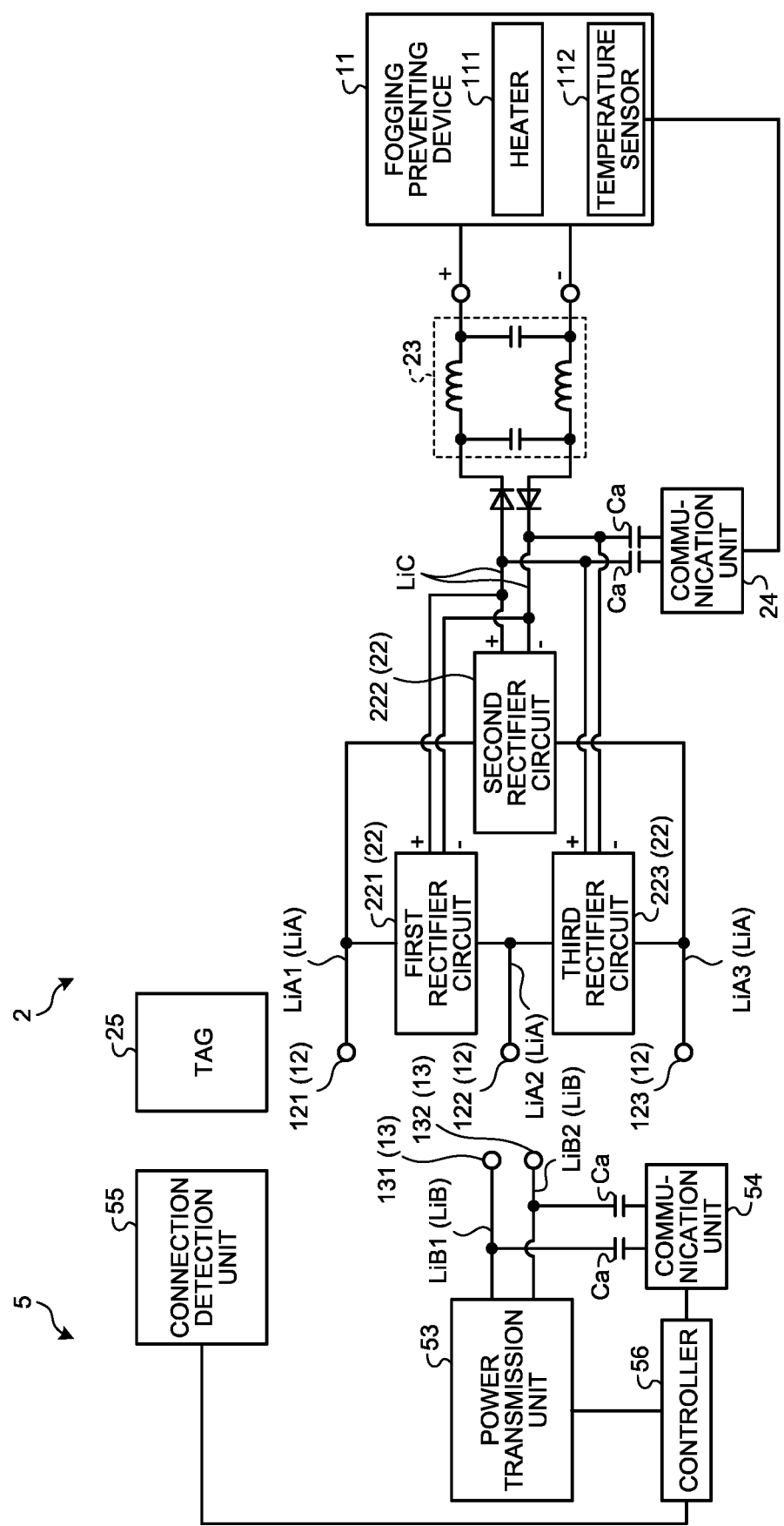
FIG. 4 is a block diagram illustrating a power feeding structure to an endoscope from a camera head.

FIG. 4 is a block diagram illustrating a power feeding structure to the endoscope 2 from the camera head 5.

As illustrated in FIG. 4, a power transmission unit 53, a communication unit 54, a connection detection unit 55, and a controller 56 are disposed inside the casing 511 of the camera head 5 (air-tight unit 51).

Figure 5:
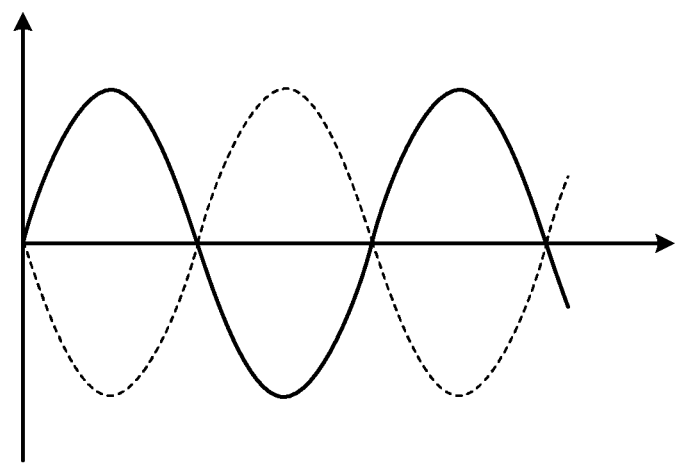
FIG. 5 is a diagram illustrating waveforms of voltages to be supplied to first and second head side terminals from a power transmission unit.

FIG. 5 is a diagram illustrating waveforms of a voltage to be supplied to the first and second head side terminals 131 and 132 from the power transmission unit 53.

The power transmission unit 53 is electrically connected to the first and second power lines LiB1 and LiB2, and under the control by the controller 56, supplies a negative sequence alternating (AC) voltage (an AC voltage of the waveform illustrated by the solid line in FIG. 5, and an AC voltage of the waveform illustrated by the broken line in FIG. 5 (waveform the phase of which is deviated by 180 degrees relative to the waveform illustrated by the solid line in FIG. 5)) to the first and second head side terminals 131 and 132.

The communication unit 54 is electrically connected to the first and second power lines LiB1 and LiB2 via a capacitor Ca for cutting the DC, and communicates with a communication unit 24, which will be described below, of the endoscope 2, by superimposing a communication signal to the AC voltage transmitted through the first and second power lines LiB1 and LiB2 (what is called power line communication) under the control by the controller 56.

For example, the communication method for the power line communication includes an orthogonal frequency division multiplexing system (OFDM system), a spectrum spread system (SS system), a multicarrier system (MC system), or the like.

The connection detection unit 55 detects the connection state of the endoscope 2 and the camera head 5 (eyepiece unit 21 and mounting unit 52). For example, the connection detection unit 55 includes a hall device, a radio frequency identification (RFID) detection circuit, and the like. The connection detection unit 55 outputs a detection signal corresponding to the detection result, to the controller 56.

The controller 56 controls an operation of the entire camera head 5 as well as the fogging preventing device 11, under the control by the control device 9.

For example, when the connection detection unit 55 detects that the endoscope 2 and the camera head 5 are connected, the controller 56 supplies a negative sequence AC voltage to the first and second head side terminals 131 and 132 from the power transmission unit 53. In other words, when the connection detection unit 55 does not detect that the endoscope 2 and the camera head 5 are connected, the controller 56 does not supply AC voltage to the first and second head side terminals 131 and 132 from the power transmission unit 53. Moreover, the controller 56 acquires the detection result of the temperature sensor 112 (temperature of the optical system) via the communication unit 54, and executes an energization control of the heater 111 so that the optical system reaches a target temperature.

As illustrated in FIG. 4, a rectifier circuit 22, a ripple filter 23, the communication unit 24, and a tag 25 are disposed in the endoscope 2 in addition to the fogging preventing device 11.

In the present embodiment, as illustrated in FIG. 4, the rectifier circuit 22 is configured by three circuits of first to third rectifier circuits 221 to 223 that are connected in parallel. For example, the first to third rectifier circuits 221 to 223 are configured by a bridge type full-wave rectifier circuit.

The first rectifier circuit 221 is electrically connected to the first and second power lines LiA1 and LiA2, and performs full-wave rectification on the AC voltage that is input between the first and second endoscope side terminals 121 and 122.

The second rectifier circuit 222 is electrically connected to the first and third power lines LiA1 and LiA3, and performs full-wave rectification on the AC voltage that is input between the first and third endoscope side terminals 121 and 123.

The third rectifier circuit 223 is electrically connected to the second and third power lines LiA2 and LiA3, and performs full-wave rectification on the AC voltage that is input between the second and third endoscope side terminals 122 and 123.

The rectifier circuit 22 then outputs a voltage on which the full-wave rectification is performed as described above, to the ripple filter 23.

Figure 6:
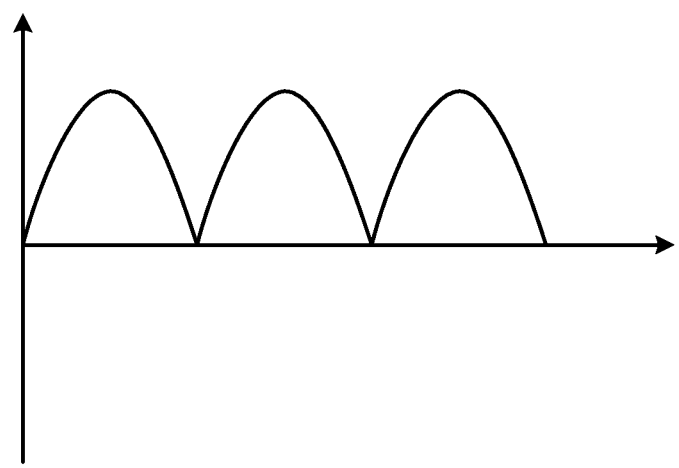
FIG. 6 is a diagram illustrating a waveform of voltage after being rectified by a rectifier circuit.
Figure 7A:
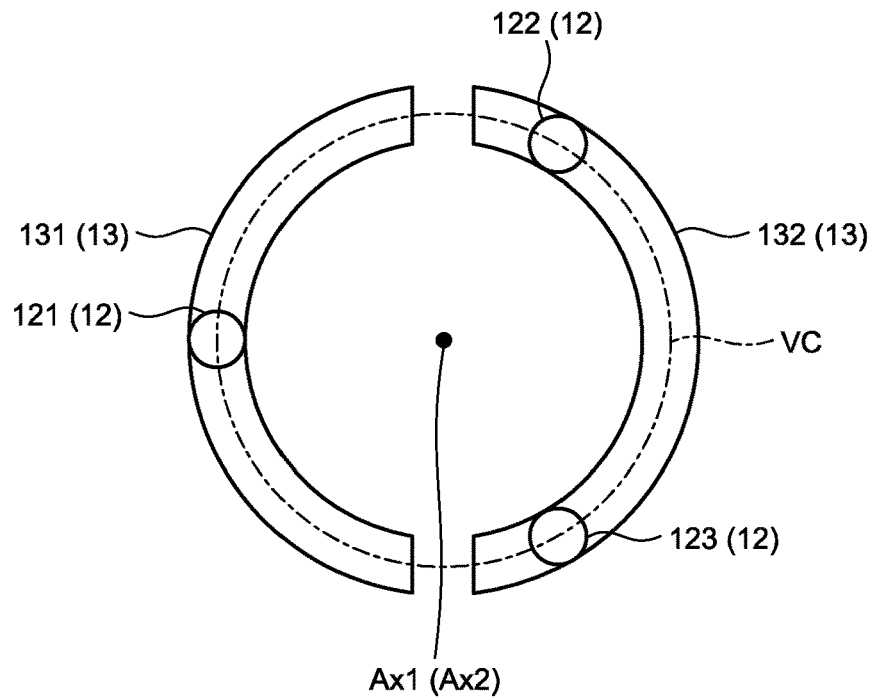
FIG. 7A is a diagram illustrating an example of a positional relation between first to third endoscope side terminals and first and second head side terminals, while the endoscope and the camera head are relatively rotated.
Figure 7B:
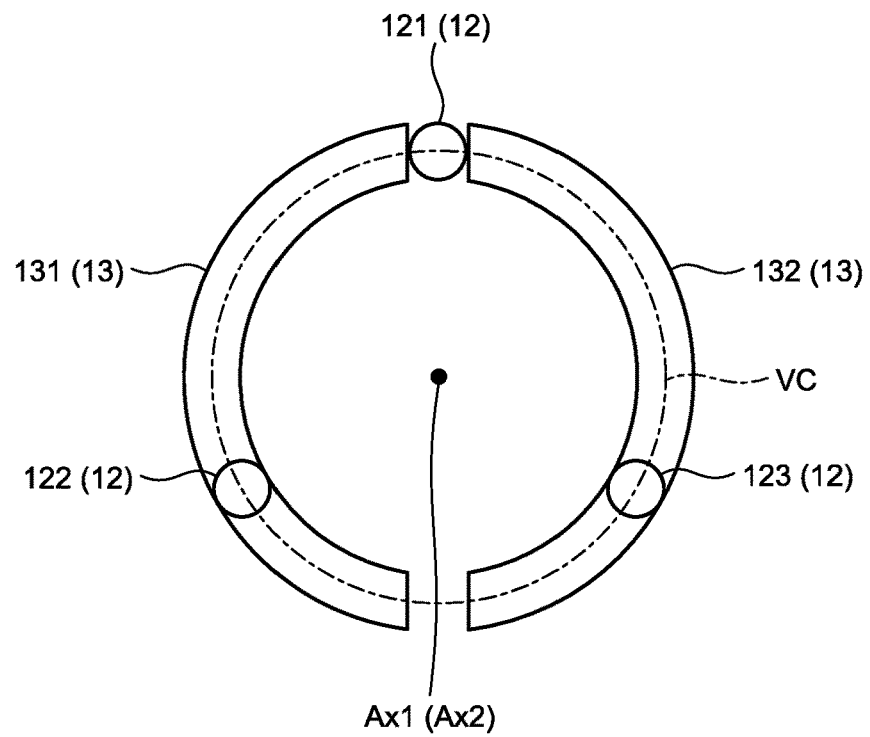
FIG. 7B is a diagram illustrating an example of a positional relation between the first to third endoscope side terminals and the first and second head side terminals, while the endoscope and the camera head are relatively rotated.

FIG. 6 is a diagram illustrating a waveform of a voltage after being rectified by the rectifier circuit 22. FIG. 7A and FIG. 7B are diagrams each illustrating an example of a positional relation between the first to third endoscope side terminals 121 to 123 and the first and second head side terminals 131 and 132, while the endoscope 2 and the camera head 5 are relatively rotated. More specifically, FIG. 7A and FIG. 7B are diagrams viewing the first to third endoscope side terminals 121 to 123 as well as the first and second head side terminals 131 to 132, from a direction along the center axis Ax1 (Ax2).

In the present embodiment, when the endoscope 2 and the camera head 5 are rotated, there are two patterns of positional relations between the first to third endoscope side terminals 121 to 123 and the first and second head side terminals 131 and 132.

As illustrated in FIG. 7A, the first pattern is a pattern in which one of the endoscope side terminals 12 and one of the head side terminals 13 are brought into contact (electrically connected) with each other, and two terminals of the endoscope side terminals 12 and one of the head side terminals 13 are electrically connected. FIG. 7A is an example of a state in which the first endoscope side terminal 121 is electrically connected with the first head side terminal 131, and the second and third endoscope side terminals 122 and 123 are electrically connected with the second head side terminal 132.

In this example, it is assumed that an AC voltage having the waveform illustrated by the solid line in FIG. 5 is supplied to the first head side terminal 131, and an AC voltage having the waveform illustrated by the broken line in FIG. 5 is supplied to the second head side terminal 132. In this case, in the first pattern illustrated in FIG. 7A, the first to third rectifier circuits 221 to 223 output a voltage having the following waveform.

An AC voltage having the waveform illustrated by the solid line in FIG. 5 is input to the first rectifier circuit 221, from the first endoscope side terminal 121 that is electrically connected to the first head side terminal 131, and an AC voltage having the waveform illustrated by the broken line in FIG. 5 is input to the first rectifier circuit 221, from the second endoscope side terminal 122 that is electrically connected to the second head side terminal 132. Consequently, the first rectifier circuit 221 outputs a voltage having the waveform illustrated in FIG. 6, by performing the full-wave rectification.

An AC voltage having the waveform illustrated by the solid line in FIG. 5 is input to the second rectifier circuit 222, from the first endoscope side terminal 121 that is electrically connected to the first head side terminal 131, and an AC voltage having the waveform illustrated by the broken line in FIG. 5 is input to the second rectifier circuit 222, from the third endoscope side terminal 123 that is electrically connected to the second head side terminal 132. Consequently, the second rectifier circuit 222 outputs a voltage having the waveform illustrated in FIG. 6, by performing the full-wave rectification.

An AC voltage having the waveform illustrated by the broken line in FIG. 5 is input to the third rectifier circuit 223, from the second endoscope side terminal 122 that is electrically connected to the second head side terminal 132, and similarly, an AC voltage having the waveform illustrated by the broken line in FIG. 5 is input to the third rectifier circuit 223, from the third endoscope side terminal 123 that is electrically connected to the second head side terminal 132. In other words, an AC voltage having the same potential is supplied to the third rectifier circuit 223. Consequently, the third rectifier circuit 223 does not function.

In this manner, in the first pattern, the voltage of the waveform illustrated in FIG. 6 is output to the ripple filter 23 from the rectifier circuit 22.

As illustrated in FIG. 7B, the second pattern is a pattern in which one of the endoscope side terminals 12 is not electrically connected to the head side terminal 13 (one of the endoscope side terminals 12 comes into contact with the projection unit 524), and the two endoscope side terminals 12 and the two head side terminals 13 are electrically connected with each other in a one-to-one manner. FIG. 7B is an example in which the first endoscope side terminal 121 is not electrically connected to the head side terminal 13 (the first endoscope side terminal 121 comes into contact with the projection unit 524), the second endoscope side terminal 122 is electrically connected to the first head side terminal 131, and the third endoscope side terminal 123 is electrically connected to the second head side terminal 132.

In this example, similar to the above, it is assumed that an AC voltage having the waveform illustrated by the solid line in FIG. 5 is supplied to the first head side terminal 131, and an AC voltage having the waveform illustrated by the broken line in FIG. 5 is supplied to the second head side terminal 132. In this case, in the second pattern illustrated in FIG. 7B, the first to third rectifier circuits 221 to 223 output a voltage having the waveforms illustrated below.

In the first and second rectifier circuits 221 and 222, the first endoscope side terminal 121 is not electrically connected to either of the first head side terminal 131 or the second head side terminal 132. Consequently, the AC voltage from the first endoscope side terminal 121 is not input to the first and second rectifier circuits 221 and 222. Thus, the first and second rectifier circuits 221 and 222 do not function.

On the other hand, an AC voltage having the waveform illustrated by the solid line illustrated in FIG. 5 is input to the third rectifier circuit 223, from the second endoscope side terminal 122 that is electrically connected to the first head side terminal 131, and an AC voltage having the waveform illustrated by the broken line in FIG. 5 is input to the third rectifier circuit 223, from the third endoscope side terminal 123 that is electrically connected to the second head side terminal 132. Consequently, the third rectifier circuit 223 outputs a voltage having the waveform illustrated in FIG. 6, by performing the full-wave rectification.

As illustrated above, in the second pattern, a voltage having the waveform illustrated in FIG. 6 (voltage having the same waveform as that of the first pattern) is output to the ripple filter 23 from the rectifier circuit 22. In other words, even if the endoscope 2 and the camera head 5 are relatively rotated to any position, a voltage having the waveform illustrated in FIG. 6 is output to the ripple filter 23 from the rectifier circuit 22.

Figure 8:
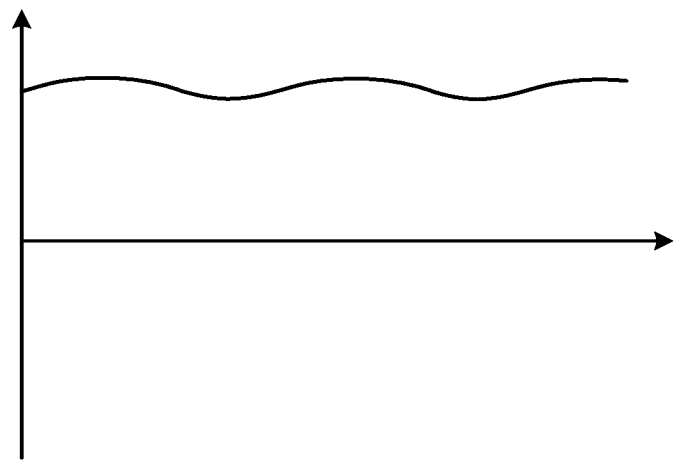
FIG. 8 is a diagram illustrating a waveform of voltage after being smoothed by a ripple filter.

FIG. 8 is a diagram illustrating a waveform of voltage after being smoothed by the ripple filter 23.

For example, the ripple filter 23 is configured of an LC filter, and smoothes the voltage output from the rectifier circuit 22. In other words, the ripple filter 23 generates a voltage having the waveform illustrated in FIG. 8, by smoothing the voltage having the waveform illustrated in FIG. 6. The smoothed voltage (direct current (DC) voltage) is supplied to the fogging preventing device 11 and the like. The fogging preventing device 11 and the like is then driven by the DC voltage.

The communication unit 24 is electrically connected to a power line LiC between the rectifier circuit 22 and the ripple filter 23 via the capacitor Ca for cutting the DC, and performs power line communication with the communication unit 54.

The tag 25 is a portion used by the connection detection unit 55 for detecting the connection state between the endoscope 2 and the camera head 5. For example, the tag 25 is made of a permanent magnet (when the connection detection unit 55 is a hall device), an RFID tag (when the connection detection unit 55 is an RFID detection circuit), and the like.

According to the embodiment described above, it is possible to achieve the following effects.

With the endoscope device 1 according to the present embodiment, the endoscope side terminals 12 and the head side terminals 13 are disposed on the same virtual circle VC, in the eyepiece unit 21 and the mounting unit 52, respectively. In other words, the endoscope side terminals 12 are not disposed side by side in the radial direction around the center axis Ax1 as in known methods. This is also same for the head side terminals 13. Consequently, there is no need to increase the diameters of the endoscope 2 (eyepiece unit 21) and the camera head 5 (mounting unit 52) in the radial direction around the center axis Ax1 (Ax2), by taking into account the arrangement of the endoscope side terminals 12 and the head side terminals 13.

Thus, the endoscope device 1 according to the present embodiment may be effectively reduced in size.

Particularly, three terminals of the endoscope side terminals 12 are disposed on the virtual circle VC. Moreover, two terminals of the head side terminals 13 are disposed on the virtual circle VC. Thus, even if the endoscope 2 and the camera head 5 are relatively rotated around the center axis Ax1 (Ax2), it is possible to implement a configuration in which the two terminals of the endoscope side terminals 12 and the two head side terminals 13 are electrically connected in a one-to-one manner. Thus, even if the endoscope 2 and the camera head 5 are relatively rotated around the center axis Ax1 (Ax2), it is possible to feed power to the endoscope 2 from the camera head 5.

Moreover, in the endoscope device 1 according to the present embodiment, the three endoscope side terminals 12 are terminals each having a convex shape and the same height. Furthermore, the two head side terminals 13 are terminals each extending in an arc shape along the virtual circle VC, and the surface of which that comes into contact with the endoscope side terminal 12 is flat and flush with the endoscope side terminal 12. Still furthermore, the mounting unit 52 includes the pressing unit 522 that presses the eyepiece unit 21 to the mounting unit 52 in the direction that the endoscope side terminal 12 comes close to the head side terminal 13.

Consequently, the plane surface formed by the tips of the three endoscope side terminals 12, and the flat surfaces of the two head side terminals 13 at the tip end side may function as the positioning surfaces of the endoscope 2 relative to the camera head 5 (the positioning surface in the center axis Ax1 (Ax2) direction, and the positioning surface around the two axes orthogonal to the center axis Ax1 (Ax2) in the rotation direction).

Particularly, for example, when four endoscope side terminals 12 are provided, the tip of one of the four endoscope side terminals 12 tends to be positioned at a position different from the plane surface formed by the tips of the other three endoscope side terminals 12. Hence, in such a case, one of the endoscope side terminals 12 needs to be configured of a movable terminal capable of moving along the center axis Ax1 (Ax2). When one of the endoscope side terminals 12 is configured of a movable terminal, it is difficult to ensure the air-tightness of the endoscope 2.

With the endoscope device 1 according to the present embodiment, the endoscope side terminals 12 are configured of three terminals as described above. Consequently, there is no need to configure the three endoscope side terminals 12 with the movable terminals, and it is possible to sufficiently ensure the air-tightness of the endoscope 2.

Furthermore, in the endoscope device 1 according to the present embodiment, the three endoscope side terminals 12 are disposed so as to be rotationally symmetric at 120 degrees around the center axis Ax1.

Consequently, the load that the three endoscope side terminals 12 receive from the mounting unit 52 (head side terminal 13 and projection unit 524) may be made equal. Consequently, it is possible to suitably maintain the positioning state of the endoscope 2 relative to the camera head 5.

Still furthermore, in the endoscope device 1 according to the present embodiment, the camera head 5 includes the power transmission unit 53 that supplies a negative sequence AC voltage to the first and second head side terminals 131 and 132. The endoscope 2 also includes the first rectifier circuit 221 that performs full-wave rectification on the AC voltage that is input between the first and second endoscope side terminals 121 and 122, and the second rectifier circuit 222 that performs full-wave rectification on the AC voltage that is input between the first and third endoscope side terminals 121 and 123. The endoscope 2 further includes the third rectifier circuit 223 that performs full-wave rectification on the AC voltage that is input between the second and third endoscope side terminals 122 and 123, and the ripple filter 23 that smoothes the voltage on which the full-wave rectification is performed by the rectifier circuit 22.

Consequently, even if the endoscope 2 and the camera head 5 are relatively rotated to any position (the first pattern and the second pattern described above), it is possible to constantly supply stable DC voltage to the fogging preventing device 11 and the like.

Particularly, for example, when the DC voltage is to be supplied to the first and second head side terminals 131 and 132, a configuration of detecting the state of the first pattern or the second pattern described above becomes necessary. Hence, the configuration tends to become complicated. On the other hand, in the present embodiment, the negative sequence AC voltage is supplied. Thus, the configuration of detecting the state of the first pattern or the second pattern becomes unnecessary. Consequently, it is possible to simplify the configuration.

Still furthermore, in the endoscope device 1 according to the present embodiment, the endoscope 2 and the camera head 5 include the communication units 24 and 54, respectively, for performing the power line communication.

Consequently, the power line for feeding power and the communication line are commonly used, and there is no need to provide a communication line in addition to the power line. Thus, it is possible to simplify the configuration of the endoscope 2 and the camera head 5.

Other Embodiment

A mode for carrying out the present disclosure has been described. However, the present disclosure is not limited to the embodiment described above.

Figure 9:
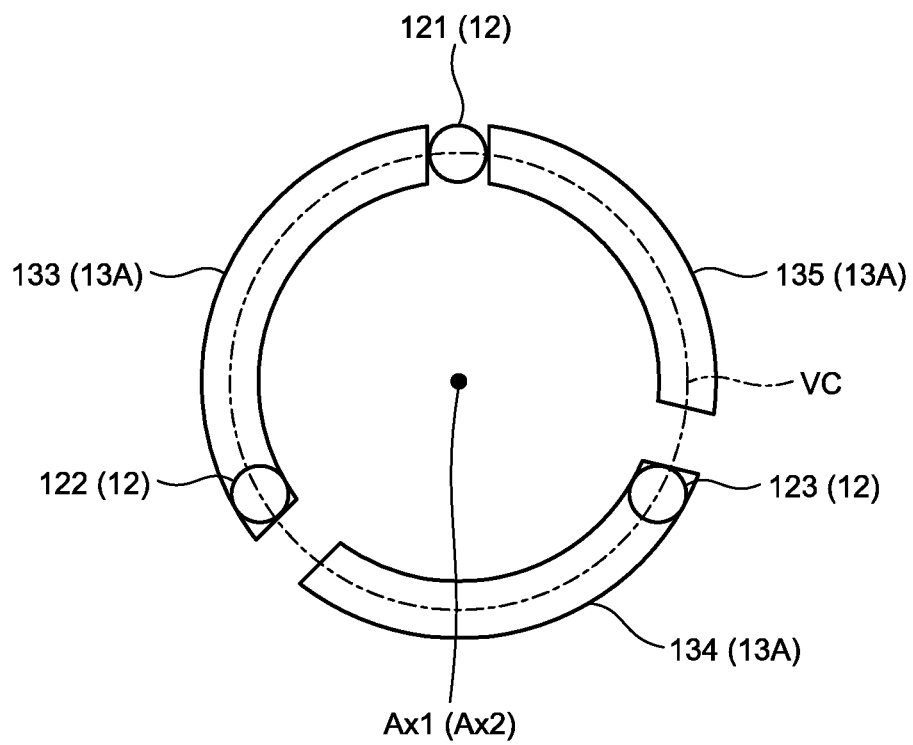
FIG. 9 is a diagram illustrating a modification of the present embodiment.

FIG. 9 is a diagram illustrating a modification of the present embodiment. More specifically, FIG. 9 is a diagram corresponding to FIG. 7A and FIG. 7B.

In the embodiment described above, the number of the endoscope side terminal 12 is different from that of the head side terminal 13. However, it is not limited thereto. For example, as illustrated in FIG. 9, the number of the head side terminals 13A may be the same as that of the endoscope side terminals 12. In other words, the head side terminals 13A may be configured of three terminals of third to fifth head side terminals 133 to 135.

In this example, the third and fourth head side terminals 133 and 134 have the same shape. Each of the third and fourth head side terminals 133 and 134 has an arc shape extending along the virtual circle VC. The surfaces of the third and fourth head side terminals 133 and 134 at the tip end side are flat and are disposed so as to be flush with each other. The fifth head side terminal 135 is formed in an arc shape extending along the virtual circle VC, but the length of the arc is set shorter than those of the third and fourth head side terminals 133 and 134. The surface of the fifth head side terminal 135 at the tip end side is flat, and is disposed so as to be flush with the surfaces of the third and fourth head side terminals 133 and 134 at the tip end side.

Although a specific illustration is omitted, the projection unit 524 described in the above embodiment is provided between the third to fifth head side terminals 133 to 135.

Figure 10:
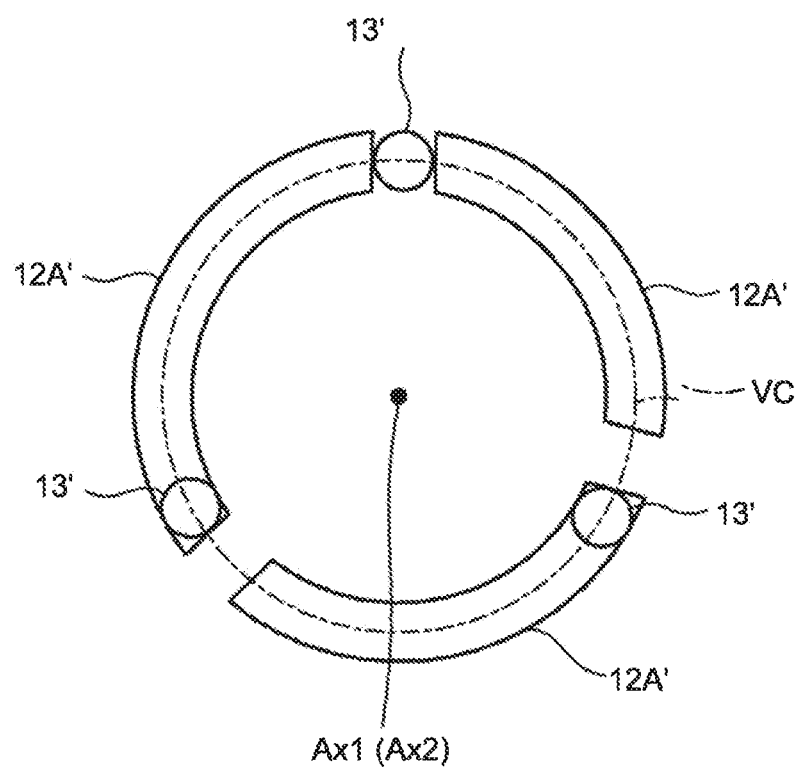
FIG. 10 is a diagram illustrating a modification of the present embodiment.

The shapes of the endoscope side terminal 12 as well as the head side terminals 13 and 13A are not limited to those illustrated in the above embodiment and FIG. 9, and contrary to those in the above embodiment and FIG. 9, the endoscope side terminal 12 may be disposed as head side terminal 13' in the camera head 5, and the head side terminals 13 and 13A may be disposed as endoscope side terminals 12A' in the endoscope 2 as shown in FIG. 10.

Moreover, the number of the endoscope side terminal 12 and the head side terminals 13 and 13A is not limited to those indicated in the above embodiment and FIG. 9, and may be another number, as long as a first one of the terminals includes at least three terminals and a second one of the terminals includes at least two terminals.

In the above embodiment, the fogging preventing device 11 receives power from the camera head 5. However, it is not limited thereto, and the other member may receive power from the camera head 5. For example, the light source device 3 and the light guide 4 may be omitted, and a light emitting diode (LED) may be provided on the tip end of the endoscope 2. The LED may then receive power from the camera head 5. Moreover, when the endoscope 2 includes an actuator for moving the optical system provided inside the endoscope 2 along the optical axis, so as to adjust the focus and angle of view, the actuator may receive power from the camera head 5.

In the above embodiment, at least a part of functions of the controller 56 may be provided outside the camera head 5 (for example, connector CN1 or CN2, and control device 9).

In the above embodiment, the endoscope 2 is not limited to the rigid endoscope but may also be a flexible endoscope.

In the above embodiment, the endoscope device 1 is not limited to be used in the medical field, but may also be used in the industrial field. The endoscope device 1 may be used as an endoscope device for observing the inside of a subject such as a machine structure and the like.

In the endoscope device, the endoscope side terminals and the head side terminals are disposed on the same virtual circle in the eyepiece unit and the mounting unit, respectively. In other words, the endoscope side terminals are not disposed side by side in the radial direction around the insertion axis as in the known method. This is also the same for the head side terminals. Consequently, there is no need to increase the diameters of the endoscope (eyepiece unit) and the camera head (mounting unit) in the radial direction around the insertion axis, by taking into account the arrangement of the endoscope side terminals and the head side terminals.

Thus, the endoscope device may be effectively reduced in size.

In particular, the first one of the endoscope side terminal and the head side terminal include at least three terminals disposed on the virtual circle. Moreover, the second one of the endoscope side terminal and the head side terminal include at least two terminals disposed on the virtual circle. Hence, even if the endoscope and the camera head are relatively rotated around the insertion axis, the two terminals of the first one of the terminals and the two terminals of the second one of the terminals are electrically connected in a one-to-one manner. Consequently, even if the endoscope and the camera head are relatively rotated around the insertion axis, it is possible to feed power to the endoscope from the camera head.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. An endoscope device, comprising:
   an endoscope adapted to be inserted into a subject, the endoscope to retrieve a subject image in the subject from a tip end, and output the subject image from an eyepiece; and
   a camera head including a mount that detachably connects the camera to the eyepiece and a power supply that outputs an AC voltage, the camera head to pick up the subject image, wherein
   the eyepiece and the mount are connected with each other so as to be able to relatively rotate the endoscope and the camera head around an insertion axis of the endoscope to be inserted into the subject,
   the eyepiece includes an endoscope side terminal,
   the mount includes a head side terminal that is electrically connected to the endoscope side terminal and that feeds power to the endoscope from the camera head,
   the endoscope side terminal includes at least three terminals disposed on a virtual circle around the insertion axis, and
   the head side terminal includes a first head side terminal and a second head side terminal disposed on the virtual circle,
   the power supply provides the AC voltage to the first head side terminal and the second head side terminal, and
   the endoscope includes a rectifier circuit that performs full-wave rectification on an AC voltage input to the endoscope side terminal.

2. The endoscope device according to claim 1, wherein
   each of the at least three terminals has a convex shape projecting toward other terminals, and
   each of the first and second head side terminals extends in an arc shape along the virtual circle, and has a flat surface brought into contact with the endoscope side terminal.

3. The endoscope device according to claim 2, wherein the endoscope side terminal includes three terminals.

4. The endoscope device according to claim 3, wherein the three terminals have a same shape and are disposed to be rotationally symmetric at 120 degrees around the insertion axis.

5. The endoscope device according to claim 2, wherein
   the at least three terminals have a same height,
   the first and second head side terminals are formed such that a surface of one of the first and second head side terminals that comes into contact with the endoscope side terminal is flush with a surface of the other one of the first and second head side terminals, and
   the mounting includes a pressing unit that presses the eyepiece to the mounting in a direction that the endoscope side terminal comes close to the head side terminal.

6. The endoscope device according to claim 1, wherein
   the endoscope side terminal is provided so as to have a different number of terminals from that of the head side terminal, the terminals have a same shape and are rotationally symmetric around the insertion axis, and
   the first and second head side terminals of the head side terminal have a same shape and are disposed so as to be rotationally symmetric around the insertion axis.

7. The endoscope device according to claim 1, wherein
   the endoscope side terminal is provided so as to have a same number of terminals as that of the head side terminal,
   one of the endoscope side terminal and the head side terminal has terminals that area same shape and are disposed so as to be rotationally symmetric around the insertion axis, and
   other of the endoscope side terminal and the head side terminal includes at least one terminal having a shape different from the other terminals.

8. The endoscope device according to claim 1, wherein
   the power supply supplies a negative sequence AC voltage to the first head side terminal and the second head side terminal, and
   the endoscope includes a ripple filter that smooths a voltage on which full-wave rectification is performed in the rectifier circuit.

9. The endoscope device according to claim 8, wherein the endoscope side terminal includes three terminals of a first endoscope side terminal, a second endoscope side terminal, and a third endoscope side terminal; and
the rectifier circuit includes
a first rectifier circuit that performs full-wave rectification on an AC voltage input between the first endoscope side terminal and the second endoscope side terminal,
a second rectifier circuit that performs full-wave rectification on an AC voltage input between the first endoscope side terminal and the third endoscope side terminal, and
a third rectifier circuit that performs full-wave rectification on an AC voltage input between the second endoscope side terminal and the third endoscope side terminal.

10. The endoscope device according to claim 1, wherein the endoscope and the camera head communicate with each other by superimposing a communication signal to the AC voltage.

11. An endoscope device, comprising:
an endoscope adapted to be inserted into a subject, the endoscope to retrieve a subject image in the subject from a tip end, and output the subject image from an eyepiece; and
a camera head including a mount that detachably connects the camera to the eyepiece and a power supply that outputs an AC voltage, the camera head to pick up the subject image, wherein
the eyepiece and the mount are connected with each other so as to be able to relatively rotate the endoscope and the camera head around an insertion axis of the endoscope to be inserted into the subject,
the eyepiece includes an endoscope side terminal,
the mount includes a head side terminal that is electrically connected to the endoscope side terminal and that feeds power to the endoscope from the camera head,
the head side terminal includes at least three terminals disposed on a virtual circle around the insertion axis, and
the endoscope side terminal includes a first endoscope side terminal and a second endoscope side terminal disposed on the virtual circle,
the power supply provides the AC voltage to the first endoscope side terminal and the second endoscope side terminal via the head side terminal, and
the endoscope includes a rectifier circuit that performs full-wave rectification on an AC voltage input to the endoscope side terminal.

12. The endoscope device according to claim 1, wherein each of the at least three terminals has a convex shape projecting toward other terminals, and
each of the first and second endoscope side terminals extends in an arc shape along the virtual circle, and has a flat surface brought into contact with the first terminal.

13. The endoscope device according to claim 12, wherein the head side terminal includes three terminals.

14. The endoscope device according to claim 13, wherein the three terminals have a same shape and are disposed to be rotationally symmetric at 120 degrees around the insertion axis.

15. The endoscope device according to claim 12, wherein the at least three terminals have a same height,
the first and second endoscope side terminals are formed such that a surface of one of the first and second head side terminals that comes into contact with the head side terminal is flush with a surface of the other one of the first and second endoscope side terminals, and
the mounting includes a pressing unit that presses the eyepiece to the mounting in a direction that the endoscope side terminal comes close to the head side terminal.

16. The endoscope device according to claim 11, wherein the head side terminal is provided so as to have a different number of terminals from that of the head side terminal,
the terminals have a same shape and are rotationally symmetric around the insertion axis, and
the first and second endoscope side terminals of the endoscope side terminal have a same shape and are disposed so as to be rotationally symmetric around the insertion axis.

17. The endoscope device according to claim 11, wherein the endoscope side terminal is provided so as to have a same number of terminals as that of the head side terminal,
one of the endoscope side terminal and the head side terminal has terminals that are a same shape and are disposed so as to be rotationally symmetric around the insertion axis, and
other of the endoscope side terminal and the head side terminal includes at least one terminal having a shape different from the other terminals.

18. The endoscope device according to claim 11, wherein the endoscope side terminal includes three terminals of a first endoscope side terminal, a second endoscope side terminal, and a third endoscope side terminal; and
the rectifier circuit includes
a first rectifier circuit that performs full-wave rectification on an AC voltage input between the first endoscope side terminal and the second endoscope side terminal,
a second rectifier circuit that performs full-wave rectification on an AC voltage input between the first endoscope side terminal and the third endoscope side terminal, and
a third rectifier circuit that performs full-wave rectification on an AC voltage input between the second endoscope side terminal and the third endoscope side terminal.

19. The endoscope device according to claim 11, the power supply supplies a negative sequence AC voltage.

20. The endoscope device according to claim 11, wherein the endoscope and the camera head communicate with each other by superimposing a communication signal to the AC voltage.

* * * * *